(12) United States Patent
Sonoi et al.

(10) Patent No.: US 8,070,842 B2
(45) Date of Patent: Dec. 6, 2011

(54) DENTAL POLISHING ARTICLE WHICH CONTAINS SPHERICAL RESIN PARTICLES

(75) Inventors: Syuji Sonoi, Kyoto (JP); Osamu Asao, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 622 days.

(21) Appl. No.: 11/920,133

(22) PCT Filed: May 10, 2006

(86) PCT No.: PCT/JP2006/309404
§ 371 (c)(1),
(2), (4) Date: Nov. 9, 2007

(87) PCT Pub. No.: WO2006/121080
PCT Pub. Date: Nov. 16, 2006

(65) Prior Publication Data
US 2009/0068614 A1    Mar. 12, 2009

(30) Foreign Application Priority Data

May 11, 2005 (JP) ................................. 2005-138131
Jun. 23, 2005 (JP) ................................. 2005-182739

(51) Int. Cl.
*C09K 3/14* (2006.01)
*B24D 3/00* (2006.01)
*B24D 11/00* (2006.01)

(52) U.S. Cl. ................ 51/298; 51/293; 51/296

(58) Field of Classification Search .................... 51/293, 51/296, 298
See application file for complete search history.

(56) References Cited

U.S. PATENT DOCUMENTS

| | | | |
|---|---|---|---|
| 1,427,503 A * | 8/1922 | Wake | 451/524 |
| 5,679,067 A * | 10/1997 | Johnson et al. | 451/527 |
| 6,277,160 B1 * | 8/2001 | Stubbs et al. | 51/295 |
| 6,383,238 B1 | 5/2002 | Takahashi et al. | |
| 6,554,614 B1 * | 4/2003 | Dubbe et al. | 433/125 |
| 2004/0005850 A1 | 1/2004 | Stepanovich | |

FOREIGN PATENT DOCUMENTS

| | | | |
|---|---|---|---|
| CN | 1284531 A | | 2/2001 |
| CN | 1473094 A | | 2/2004 |
| JP | 10-188237 | * | 7/1998 |
| JP | 20019736 | | 1/2001 |
| JP | 2001198836 | | 7/2001 |
| JP | 2002146344 | | 5/2002 |
| JP | 200522033 | | 1/2005 |

OTHER PUBLICATIONS

Machine Translation of JP 10-188237 Jul. 1998.*

* cited by examiner

*Primary Examiner* — Shuangyi Abu Ali
(74) *Attorney, Agent, or Firm* — Novak Druce + Quigg LLP

(57) ABSTRACT

The present invention provides a dental polishing article having excellent polishability, which can polish dental composite resin, porcelain, dental restorative and prosthetic materials and teeth at a low cost, conveniently in a short time. More specifically, the present invention provides a dental polishing article which comprises a polishing portion formed by compounding polishing grains in an elastomer binder, and the polishing portion further comprising spherical resin particles.

4 Claims, 2 Drawing Sheets

DENTAL POLISHING ARTICLE WHICH CONTAINS SPHERICAL RESIN PARTICLES

TECHNICAL FIELD OF THE INVENTION

The present invention relates to a polishing article which can polish dental restorative and prosthetic materials and teeth effectively, conveniently and easily at a low cost. More specifically, the present invention relates to a technique for reducing an amount of expensive diamond grains to be compounded in a polishing article.

BACKGROUND ART

In dental treatment, when diseases such as caries exist in teeth, they are eliminated and a variety of materials such as metals, dental composite resin, porcelain and the like are used to restore the eliminated parts. Particularly, dental composite resin and porcelain are greatly demanded because they are excellent in esthetic due to exhibition of a dental crown color.

However, these dental restorative and prosthetic materials having high esthetic are hard to be polished. Particularly, dental composite resin is composed of glass filler having high hardness and resin having low hardness. It is very difficult to varnish materials composed of a plurality of materials having different hardness each other at a final polishing stage.

In addition, it is also difficult to varnish by polishing porcelain and teeth due to high hardness.

JP 11-277453A discloses a dental polishing article composed of a buffing material in which cerium grains are fixed to its polishing portion. This means is excellent in fitness, elasticity and flexibility of the polishing portion. However, its application is limited to dental porcelain and it cannot be use for materials to be polished.

In many of current polishing method, polishing is carried out with an elastomer polishing article after adjusting shapes and occlusion with a grinding instrument such as vitrified bonds or electroplated diamond tools.

Since these methods cannot achieve sufficient gloss, varnishing is carried out by using a cup-shape rotary instrument made of rubber and the like or a brush made of nylon with supplying special polishing paste. However, this method of varnishing takes very long time and is ineffective for treatment. A chair time for patients tends to expand.

In addition, by using diamond grains, it is relatively easy to varnish these hard materials to be polished, and diamond-containing elastomer polishing articles are commercially available.

For example, JP 6-22983A discloses a technique to improve polishability by kneading coated diamond grains with elastomer and by molding.

JP 2005-22033A discloses a technique to improve polishability by forming hollows or holes in a polishing portion in order to suppress friction when polishing. However, components used in the polishing portion is usual and when materials having high hardness is polished, it is required to use diamond as grains.

JP 2001-9736A discloses a porous polishing article having moderate flexibility and a hardwearing property in which bubbles are formed in the polishing portion.

However, since these polishing articles contain a lot of diamond, they are very expensive. Thus, polishing articles using reduced amount of diamond have been demanded.

JP 2002-86361A discloses polishing articles made by compounding inorganic fibers in elastomer. Compounding of inorganic fibers improves polishability and reduces the amount of grains to be used. However, when they are used in dental composite resin, it is not so useful because they scratch the resin surface.

[Patent Document 1] JP 11-277453A
[Patent Document 2] JP 6-22983A
[Patent Document 3] JP 2005-22033A
[Patent Document 4] JP 2001-9736A
[Patent Document 5] JP 2002-86361A

DISCLOSURE OF THE INVENTION

Problem to be Solved by the Invention

The object of the present invention is to provide a dental rotational polishing article which has excellent polishability on dental composite resin, porcelain and teeth, and can easily polish them at a low cost and in a short time.

The present invention provides, in particular, a polishing article capable of polishing hard materials to be polished which are dental restorative and prosthetic materials having high esthetic while reducing an amount of expensive diamond grains.

Means for Solving the Problem

The present invention is a dental polishing article having a polishing portion in which polishing grains are compounded in an elastomer binder and is characterized in that the polishing portion contains spherical resin particles.

The polishing article of the present invention comprises a polishing portion and a shank portion for attaching to a dental hand piece or a chuck for a shank.

The polishing article 1 of the present invention may be those formed by integrating a polishing portion 10 and a shank portion 20 which is a standardized parts used for dental polishing articles as shown in FIG. 1a, or snap-on type ones having a chuck for a shank 30 which is attachable and detachable to the shank portion 20.

The polishing portion 10 in the polishing article of the present invention may be formed by any known methods which mold raw materials prepared by homogeneously kneading an elastomer binder 11, polishing grains 12 and spherical resin particles 13.

In addition, a shape of the polishing portion 10 is not particularly limited but is a shape which can fit to the geometry of tooth surfaces, for example, a wheel shape, a bullet shape, a disc shape, a cup shape and the like.

The elastomer binder 11 used in the dental polishing article 1 of the present invention is at least one kind of organic elastomer selected from organic elastomer having a rubber hardness of 30 to 80.

In the present invention, as the elastomer binder, at least one of synthetic or natural rubbers having elasticity, such as silicone rubber, urethane rubber, chloroprene rubber, nitrile rubber, butadiene rubber, butyl rubber, styrene-butadiene rubber, ethylene-butadiene rubber, fluorine rubber and the like may be used. It is preferable to use silicone rubber or urethane rubber.

The polishing grains 12 used in the dental polishing article 1 of the present invention are at least one kind of polishing particles having a Mohs hardness of 9 or harder.

In the present invention, as the polishing grains, diamond, boron nitride, aluminium oxide, silicon carbide may be used. It is preferable to use diamond or boron nitride.

The spherical resin particles 13 used in the dental polishing article 1 of the present invention are spherical particles manufactured by suspension polymerization or emulsion polymerization rather than irregular-shaped particles manufactured by pulverizing a lump of resin. By using these polymerization methods, particles which are defined with a curved surface, have few inflection points and have no sharp angle are obtained.

In the present invention, as the spherical resin particles, at least one from acrylic, styrene, nylon, polyethylene, phenol, melamine, urethane resins may be used.

Since the elastomer binder 11 used in the polishing portion of the dental polishing article 1 of the present invention contains a foaming agent, the obtained polishing portion 10 of the dental polishing article 1 of the present invention is porous.

In the present invention, as the foaming agent, at least one of organic or inorganic compounds such as dinitrosopentamethylenetetramine (DPT), azodicarbonamide (ADCA), 4,4'-oxybisbenzensulfonylhydrazide (OBSH) and sodium hydrogencarbonate can be used.

Effect of the Invention

According to the present invention, a dental polishing article may be provided which can easily polish not only dental composite resin but also porcelain and teeth and is capable of reducing a cost by decreasing the amount of expensive polishing grains.

More specifically, compounding of spherical resin particles provides excellent polishability and decreases an amount of expensive grains such as diamond to reduce a production cost.

Further, a porous polishing portion may be obtained by adding a foaming agent in an elastomer binder and, thus, fitness between the polishing portion and materials to be polished improves and an effect of polishing enhances and hardness of the polishing portion becomes adjustable.

BEST MODE FOR CARRYING OUT THE INVENTION

Figure 1:
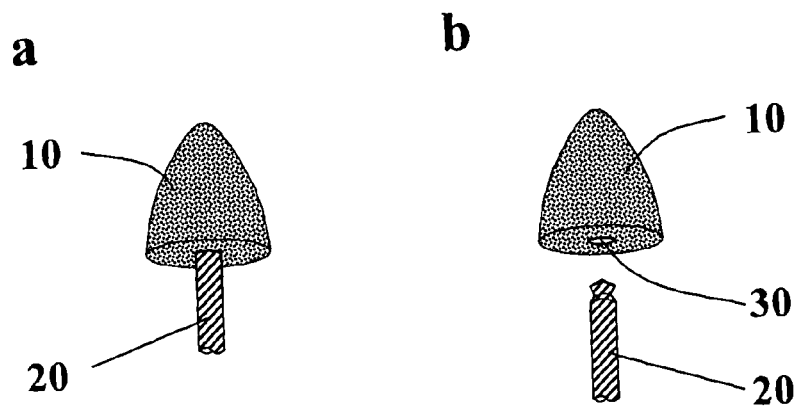
FIG. 1 A schematic illustration showing one type of the polishing article (bullet-shaped) of the present invention.

The polishing portion 10 constituting the polishing article 1 of the present invention is formed by any known method, for example, heating such as hot pressing which molds a polishing material obtained by mixing and kneading the elastomer binder 11 with the polishing grains 12 such as diamond and the spherical resin particles 13 into a desired shape for a polishing portion.

In the present invention, polishing grains 12 having an average particle size of 0.05 to 20 μm and spherical resin particles 13 having an average particle size of 0.5 to 100 μm may be used in combination with the above elastomer binder 11.

The polishing portion of the first embodiment of the present invention is formed by using a polishing material in which polishing grains and spherical resin particles much larger than the polishing grains are compounded in an elastomer binder.

Polishing grains having an average particle size of 1 to 6 μm and one or more types of resin particles having an average particle size of 10 to 100 μm, which is larger than that of the polishing grains, are combined to provide excellent polishability.

Particularly, in the polishing portion of this embodiment, 50 to 200 parts by weight of polishing grains having a particle size of 1 to 6 μm and 50 to 150 parts by weight of spherical resin particles having a particle size of 10 to 100 μm are compounded relative to 100 parts by weight of the binder.

The polishing portion of the second embodiment of the present invention is formed by using a polishing material in which polishing grains and spherical resin particles much smaller than the polishing grains are compounded in an elastomer binder.

Polishing grains having an average particle size of 10 to 20 μm and one or more types of resin particles having an average particle size of 0.5 to 10 μm, which is smaller than that of the polishing grains, are combined to provide excellent polishability.

Particularly, in the polishing portion of this embodiment, 50 to 200 parts by weight of polishing grains having a particle size of 10 to 20 μm and 50 to 150 parts by weight of spherical resin particles having a particle size of 0.5 to 10 μm are compounded relative to 100 parts by weight of the binder.

The spherical resin particles used in the present invention is characterized in that their circularity is within a range from 0.9 to 1.0, preferably 0.95 to 1.00.

Circularity of a resin particle was obtained by processing images of scanning electron microscopy (SEM) with an image analyzer. The number of images to be analyzed was 50 or more.

When an area of a particle obtained by image processing is denoted by S and a perimeter of the particle is denoted by L, the circularity e is represented by the following expression.

$$e = (4 \cdot \pi \cdot S)/(L^2)$$

EXAMPLES

The embodiments of the present invention will be explained below with referring to Examples.

Polishing materials obtained by mixing the contents shown in Table 1 were molded by hot pressing at 150° C. for 10 minutes into a bullet shape to form polishing articles of Examples 1 to 4 and Comparative Examples 1 to 4.

Evaluation was performed by polishing a surface of dental composite resin specimens at 7,500 rpm for 30 seconds at about 1 N load with each of the polishing articles fixed to a shaft special for a dental hand piece engine to rank workability (touch at polishing), polishability, durability based on the following criteria.

The specimens were prepared as follows. First, a stainless ring with an inner diameter of 15 mm and a thickness of 2 mm was placed on a glass slide. Dental composite resin (Beautifil Flow, Shofu Inc.) was filled in the ring and another glass slide was placed on it. The resin was cured from both sides for 3 minutes each with a dental photopolymerization irradiator (TwinCure, Shofu Inc.) to obtain a cylindrical specimen.

In addition, gloss values on the polished surface of the specimens were measured according to a specular gloss measurement method defined in JIS Z 8741.

(1) Workability

Sensory evaluations were carried out at polishing to rank polishing materials based on the following criteria.

[Criteria for Evaluation]

A: Very good

A touch at polishing is soft. No vibrations and no obstacles occur. Polishing progresses very smoothly.

B: Good

A touch at polishing is soft. Few vibrations and few obstacles occur. Polishing progresses smoothly.

C: Fair

A touch at polishing is moderate. Some vibrations and some obstacles occur. Polishing progresses without problem.

D: Poor

A touch at polishing is hard. Vibrations and obstacles occur. Polishing does not progress smoothly.

E: Very poor

A touch at polishing is hard. Vibrations and obstacles occur. Polishing is difficult.

(2) Polishability

Amounts eliminated from specimens at polishing were measured to rank polishing materials based on the following criteria.

[Criteria for Evaluation]

A: Very good

The amount eliminated from the specimen is 0.3 mg or more.

B: Good

The amount eliminated from the specimen is 0.2 to 0.3 mg.

C: Fair

The amount eliminated from the specimen is 0.1 to 0.2 mg.

D: Poor

The amount eliminated from the specimen is 0 to 0.1 mg.

E: Very poor

The amount eliminated from the specimen is 0 mg.

(3) Durability

Amounts worn from polishing articles at polishing were measured to rank polishing materials based on the following criteria.

[Criteria for Evaluation]

A: Very good

The amount worn from the polishing article is 0.5 mg or less.

B: Good

The amount worn from the polishing article is 0.5 to 1.0 mg.

C: Fair

The amount worn from the polishing article is 1.0 to 1.5 mg.

D: Poor

The amount worn from the polishing article is 1.5 to 2.0 mg.

E: Very poor

The amount worn from the polishing article is 2.0 mg or more.

(4) Gloss on Polished Surfaces

Gloss values were measured according to a specular gloss measurement method defined in JIS Z 8741.

The First Embodiment

Figure 2:
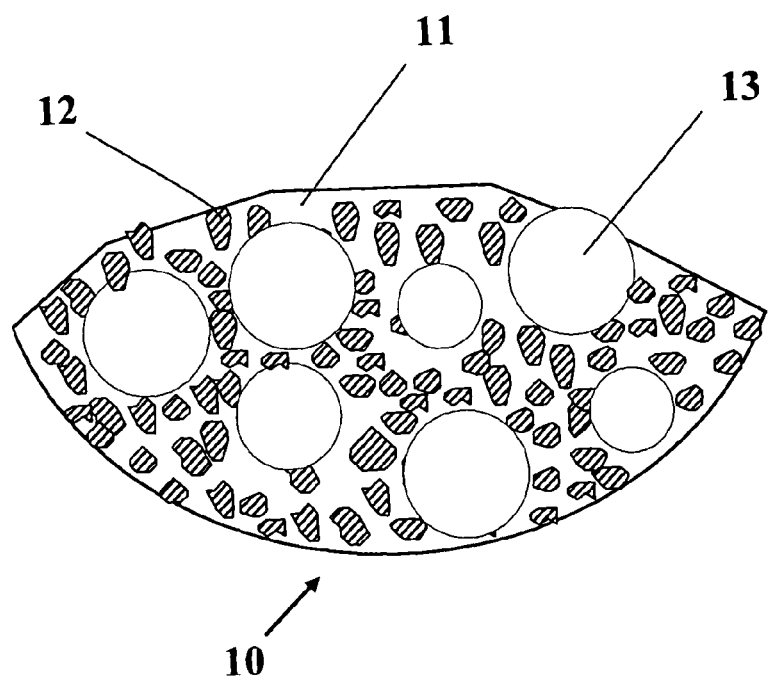
FIG. 2 A cross-sectional view of the polishing portion of the first embodiment of the present invention.

A cross-sectional view of the polishing portion 10 of the first embodiment of the present invention is shown in FIG. 2. The polishing portion 10 is formed by using a polishing material in which diamond grains 12 and acrylic resin particles 13 much larger than the diamond grains are compounded in an elastomer binder 11.

Since the acrylic resin particles 13 much larger than the diamond grains 12 are compounded, high polishability is achieved in spite of the particle size of the diamond grains 12 being small.

Example 1 explains a polishing article 1 comprising a polishing portion 10 in which 2 to 4 μm of diamond was used as polishing grains 12 and spherical acrylic resin particles having an average particle size of 60 μm and 100 μm were compounded in a silicone resin elastomer binder 11 (TSE3450, GE Toshiba Silicones Co., Ltd).

Comparing with a polishing article of Comparative Example 1 in which spherical acrylic resin particles were not compounded, durability, workability (touch at polishing) as well as finishing after polishing (gloss) improved.

Example 1 achieved a finishing surface more excellent than Comparative Example 2 in which a lot of diamond grains were compounded. Thus, a cost can be reduced because expensive diamond is not used so much.

In Example 1, the spherical acrylic resin particles having an average particle size of 60 μm and those having an average particle size of 100 μm were compounded at a ratio of 1:1. Spherical resin particles having different particle sizes may be combined to adjust polishability and workability.

In addition, since spherical resin particles having circularity of 0.95 or higher were used in Example 1, with comparing with Comparative Example 3 in which irregular-shaped particles having circularity of 0.72 were used, there was no difference in workability and durability but the gloss value was significantly higher.

Example 2 explains a polishing article in which a foaming agent DPT was added to the elastomer binder 11 in Example 1. Addition of a foaming agent resulted in a porous polishing portion by foaming when the raw materials were molded by hot pressing.

Thereby, the polishing article became soft and a state of contact between the polishing article and the materials to be polished became better to improve workability and gloss of the finishing surface. Very high effect was exhibited.

The Second Embodiment

Figure 3:
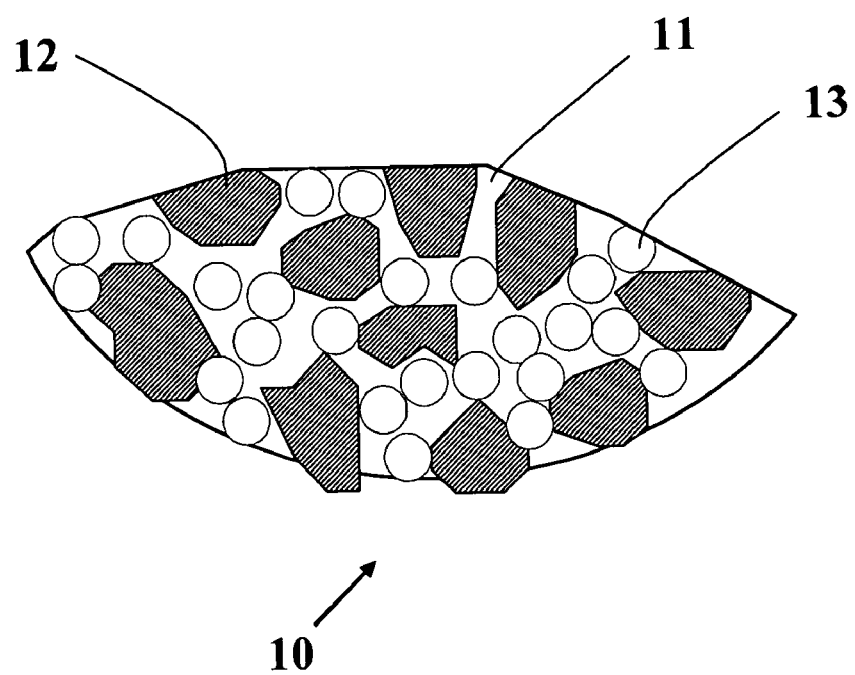
FIG. 3 A cross-sectional view of the polishing portion of the second embodiment of the present invention.

A cross-sectional view of the polishing portion 10 of the second embodiment of the present invention is shown in FIG. 3. The polishing portion 10 is formed by using a polishing material in which diamond grains 12 and acrylic resin particles 13 much smaller than the diamond grains are compounded in an elastomer binder 11.

Since fine acrylic resin particles are mixed with relatively coarse diamond particles, the acrylic resin particles behaves as absorbers for the grains and varnishes the polished surface to achieve an excellent finishing surface while having high polishability.

Example 3 explains a polishing article 1 in which 10 to 20 μm of diamond grains 12 was used and spherical acrylic resin particles having an average particle size of 2 μm were compounded in an elastomer binder 11 (TSE3450, GE Toshiba Silicones Co., Ltd).

Comparing with a polishing article of Comparative Example 4 in which spherical acrylic resin particles were not compounded, workability and characteristics of the finishing surface after polishing improved.

Example 4 explains a polishing article in which a foaming agent DPT was added to the elastomer binder 11 in Example 3. Addition of a foaming agent resulted in a porous polishing portion by foaming when the raw materials were molded by hot pressing.

Thereby, the polishing article became soft and a state of contact between the polishing article and the materials to be polished becomes better to improve workability and gloss of the finishing surface. Very high effect was exhibited.

In addition, the above polishing articles formed according to the present invention can exhibit effects similar to the above-mentioned effects on porcelain and teeth.

TABLE 1

Contents and evaluation results of polishability for the polishing portion of the first embodiment

| | | Ex. 1 | Comp. Ex. 1 | Comp. Ex. 2 | Comp. Ex. 3 | Ex. 2 |
|---|---|---|---|---|---|---|
| Contents (part by weight) | Silicone resin | 100 | 100 | 100 | 100 | 100 |
| | Diamond particle Avg. part. size: 2-4 μm | 140 | 140 | 200 | 140 | 140 |
| | Acrylic resin particle Avg. part. size: 60 μm Circularity: 0.97 | 42 | — | — | — | 42 |
| | Acrylic resin particle Avg. part. size: 100 μm Circularity: 0.96 | 42 | — | — | — | 42 |
| | Melamine resin particle Avg. part. size: 150 μm Circularity: 0.72 | — | — | — | 100 | — |
| | Foaming agent | — | — | — | — | 2.8 |
| Properties | Workability | A | D | D | B | B |
| | Durability | B | E | E | B | B |
| | Polishability | B | D | A | B | B |
| | Gloss: Gs(60°) | 47.1 | 8.8 | 35.0 | 15.6 | 55.8 |

TABLE 2

Contents and evaluation results of polishability for the polishing portion of the second embodiment

| | | Ex. 3 | Ex. 4 | Comp. Ex. 4 |
|---|---|---|---|---|
| Contents (part by weight) | Silicone resin | 100 | 100 | 100 |
| | Diamond particle Avg. part. size: 10-20 μm | 140 | 140 | 140 |
| | Acrylic resin particle Avg. part. size: 2 μm Circularity: 0.98 | 56 | 56 | — |
| | Foaming agent | — | 2.8 | — |
| Properties | Workability | B | A | C |
| | Durability | B | B | E |
| | Polishability | A | A | B |
| | Gloss: Gs(60°) | 39.3 | 41.5 | 22.9 |

What we claimed is:

1. A dental polishing article which comprises a polishing portion formed by compounding polishing grains in an elastomer binder, and the polishing portion further comprising spherical resin particles having circularity within a range from 0.9 to 1.0, the circularity e being represented by the expression:

$$e = (4 \cdot \pi \cdot S)/(L^2)$$

wherein S denotes an area of the particle and L denotes a perimeter of the particle, wherein the polishing portion contains 50 to 200 parts by weight of polishing grains having a particle size of 1 to 6 μm and 50 to 150 parts by weight of spherical resin particles having a particle size of 10 to 100 μm relative to 100 parts by weight of the binder or wherein the polishing portion contains 50 to 200 parts by weight of polishing grains having a particle size of 10 to 20 μm and 50 to 150 parts by weight of spherical resin particles having a particle size of 0.5 to 10 μm relative to 100 parts by weight of the binder, and wherein the polishing grains are diamond grains and the spherical resin particles are acrylic, styrene, nylon, polyethylene, phenol, melamine, or urethane resin particles.

2. The dental polishing article according to claim 1, wherein the polishing portion is porous.

3. The dental polishing article according to claim 1, wherein the circularity is within a range from 0.95 to 1.0.

4. The dental polishing article according to claim 3, wherein the polishing portion is porous.

* * * * *